United States Patent [19]

Zeiger

[11] Patent Number: 5,310,894
[45] Date of Patent: May 10, 1994

[54] SOLID PHASE POLYNUCLEOTIDE SYNTHESES

[75] Inventor: Allen R. Zeiger, Philadelphia, Pa.

[73] Assignee: Thomas Jefferson University, Philadelphia, Pa.

[21] Appl. No.: 25,891

[22] Filed: Mar. 3, 1993

Related U.S. Application Data

[60] Continuation of Ser. No. 666,342, Mar. 8, 1991, abandoned, which is a division of Ser. No. 581,063, Sep. 11, 1990, Pat. No. 5,021,550.

[51] Int. Cl.$^5$ .......................................... C07H 21/04
[52] U.S. Cl. .................................. 536/25.3; 536/25.4; 536/25.41
[58] Field of Search .................... 536/25.3, 25.4, 25.41

[56] References Cited

PUBLICATIONS

Caruthers, Science, vol. 230, 1985, pp. 281–285.
Itakura et al., Ann. Rev. Biochem, 1984, vol. 53, pp. 323–356.
Gait, "Olyonucleotide Synthesis: A Practical Approach" 1984, IRL Press, pp. 1–22.

Primary Examiner—Richard A. Schwartz
Assistant Examiner—David Guzo
Attorney, Agent, or Firm—Woodcock Washburn Kurtz Mackiewicz & Norris

[57] ABSTRACT

Methods for solid-state synthesis of polymers, especially polypeptides and polynucleotides, are provided. In accordance with a preferred embodiment, selectively activatable and reactive bonding moieties are covalently bonded to solid supports for polynucleotide and polypeptide syntheses. Products of failed reactions and some side products are caused to react with the selectively activatable and reactive bonding moiety to cause divalent bonding of unwanted products to the solid support. Upon cleavage of the initial situs of covalent bonding to the solid support, desired products are free to be collected while unwanted products remain covalently bonded to the support. Ease of purification of such polymers is a principal object of the present invention. The methods of the invention are amenable to automation and digital control and novel solid supports, activatable, reactive bonding moieties and other compositions are presented. The expression of polynucleotides prepared in accordance with preferred embodiments produces novel polypeptides.

11 Claims, No Drawings

SOLID PHASE POLYNUCLEOTIDE SYNTHESES

This is a continuation of application Ser. No. 07/666,342, filed Mar. 8, 1991, now abandoned, which is a division of application Ser. No. 581,063, filed Sep. 11, 1990, now U.S. Pat. No. 5,104,550.

FIELD OF THE INVENTION

This invention is directed to methods for the preparation of peptides, nucleotides and other complex, polymeric molecules. More particularly, solid phase syntheses of biologically important molecules and other species are provided which yield products of relatively high purity and uniformity of structure. Additionally, the methods of the present invention provide solid phase synthesis which lead to ease of synthesis and purification while avoiding unnecessary sequences of reaction steps, high costs, and mediocre yields. While manual implementation of the present invention is both straightforward and efficient, the present methods and schemes are amenable to implementation through the use of a general purpose digital computer, through the use of analog devices, through the use of special purpose digital computers and through the use of various other forms of automation.

Solid supports and novel synthetic reagents and protocols useful in the practice of the present invention are also provided as are biological mechanisms for production of novel polypeptides.

BACKGROUND OF THE INVENTION

Solid phase synthesis has been known for some time for use in the preparation of peptides and other oligomers such as nucleotides. Such solid phase synthesis makes use of an insoluble resin support for a growing oligomer. A sequence of sub-units, destined to comprise a desired polymer, are reacted together in sequence on the support. A terminal amino acid, nucleotide or other residue is attached to the solid support in an initial reaction, either directly or through a keying agent. The terminal residue is reacted, in sequence, with a series of further residues such as amino acids or blocked amino acid moieties to yield a growing oligomer attached to the solid support through the terminal residue. At each stage in the synthetic scheme, unreacted reactant materials are washed out or otherwise removed from contact with the solid phase. The cycle is continued with a pre-selected sequence of residues until the desired polymer has been completely synthesized, but remains attached to the solid support. The polymer is then cleaved from the solid support and purified for use. The foregoing general synthetic scheme was developed by R. B. Merrifield for use in the preparation of certain peptides. It has also been adapted for the preparation of oligo and poly nucleotides.

These schemes are known to persons having ordinary skill in the art. See Merrifield's Nobel Prize Lecture "Solid Phase Synthesis", *Science*, Vol. 232, pp. 341-347 (1986), incorporated herein by reference. They have also been widely reviewed. See, for example, "Solid-Phase Peptide Synthesis", Doscher, in *Methods in Enzymology*, Volume 47, *Enzyme Structure Part E*, pp. 578-617, Academic Press (1977); "Solid-Phase Peptide Synthesis", Erickson and Merrifield in *The Proteins*, Third Edition, Volume 2, at pp. 255-527, Neurath et al, ed., Academic Press (1976); Stewart, "Solid Phase Peptide and Protein Synthesis" in Solid Phase Biochemistry, Scouten, ed., Chapter 10, pp. 507-534 Wiley (1983); and *Solid Phase Peptide Synthesis,* 2nd ed., Stewart & Young, Pierce Chem. Co. (1984) which are incorporated herein by reference.

It is also known to prepare polynucleotides from nucleotide or blocked nucleotide moieties through solid phase synthesis. Such methods are analogous in concept to the synthetic methods for polypeptides and are, similarly, known to persons of ordinary skill in the art. See, for example, Ike-hara, Ohtsuka and Markham, *Adv. Carbohydrate Chem. Biochem.,* 36: 35-213 (1979); "Solid Phase Synthesis and Biological Applications of Polydeoxyribonucleotides", Wallace et al. in *Solid Phase Biochemistry,* Scouten ed., ibid., pp. 661-663. The foregoing are incorporated herein by reference.

A major disadvantage of solid phase synthetic methods for the preparation of oligomeric materials such as peptides and nucleotides results from the fact that the reactions involved in the scheme are imperfect; no reaction proceeds to 100% completion. As each new subunit is added to the growing oligomeric chain a small, but measurable, proportion of the desired reactions fails to take place. The result of this is a series of peptides, nucleotides, or other oligomers having deletions in their sequence. This problem is particularly acute for the addition of valine and aspartic acid amino acid moieties to peptide chains. The result of the foregoing imperfection in the synthetic scheme is that as desired chain length increases, the effective yield of desired product decreases drastically, since increased chances for deletion occur. Similar considerations attend other types of side reactions, such as those resulting from imperfect blocking, side reactions, and the like.

Of equal, if not greater, significance, is the fact that the increasing numbers of undesired polymeric species which result from the failed individual reactions produce grave difficulties in purification. Thus, for example, if a polypeptide is desired having 100 amino acid residues, it can be seen that there may be as many as 99 separate peptides having one deleted amino acid residue and an even greater possible number of undesired polymers having two or more deleted residues, side reaction products and the like. While each of the undesired peptides may comprise but a small proportion of the overall mole percentage of product, taken in sum the impurities attain a substantial percentage. Moreover, since their structure is very similar to that of the desired peptide, the difficulties of purifying the desired peptide from the melange becomes formidable. Similar difficulties attend the preparation of polynucleotides from their constituent nucleic acids or nucleotides.

The foregoing difficulties are exacerbated by the fact that in traditional solid state synthetic schemes, the resulting oligomer, such as a peptide or polynucleotide, is not generally purified until the synthetic scheme is completed and the product mixture removed from the solid support. Some workers, including Merrifield himself, have attempted to overcome this difficulty in the preparation of polypeptides by attaching the terminal amino acid group to the solid support with a selective, cleavable group such as one which is photolabile. After elaboration of 15 to 20 amino acid residues, the growing polypeptide chains are cleaved from the solid support, subjected to purification, and only the desired intermediate products caused to become reattached to a solid support for further elaboration of structure. Theoretically, this technique could be repeated several times to prepare large polypeptides. In actuality, however, the selective cleavage and reattachment of growing polypeptide chains from and to solid supports proceeds with only a low yield. Thus, the overall yield of polypeptide in accordance with these schemes is poor; the yield decreases with increasing peptide size. Similar difficulties are known for polynucleotides.

Another technique which has received wide acceptance in the preparation of peptides enjoys the benefit of simplicity. In accordance with this technique, each peptide bond formation reaction is repeated twice, and even more often for particularly difficult amino acids, in order to improve the overall yield of each step. While deletion of amino acid residues is substantially diminished through the use of this technique, it is not eliminated and is slow, time consuming, and costly.

Yet another approach has been to remove aliquots of the growing, solid supported, peptide or other oligomeric chain, to test the same for purity through a variety of characterization protocols and to take appropriate chemical steps to ensure high completeness in the reaction scheme. This approach is also laborious, time consuming and costly.

Yet another approach has been followed which approximates the concept of parallel synthesis known to organic chemists. Thus, some workers have prepared moderately sized peptides, i.e. about 15 amino acid units, which can successfully be purified without excessive difficulty. These segments are then assembled through traditional wet or solid-phase chemistry into the desired, larger peptide. While attractive in theory, this technique has not been shown to be particularly useful. Moderately sized polypeptides may attain a variety of conformations, certain of which are believed to inhibit the effective reaction of those segments with the desired, adjacent segments in the overall polypeptide. The result of this is generally poor yields. Similar attempts have also been made in nucleic acid synthesis without notable success.

Evidence of the long-felt need for improved methods to attain higher purity in solid-state synthesis of proteins is reflected inter alia, in "Affinity and Carrier-Mediated Peptide Purification", Wilchek and Miron, *Peptides, Structure and Function,* (1979), E. Gross and J. Meienhofer, Eds., Pierce Chem. Co., Rockford, Ill., pp. 49–57; and "Solid Phase Peptide Synthesis", Merrifield et al, ibid., pp. 29–47. Further pressure to attain solutions to the purification problems attendant to solid phase synthesis of proteins has arisen from the competing technology of genetic engineering. See "Proteins to Order", Tucker, *High Technology,* December 1985; pp. 26–34; and "Protein Engineering, Biotechnology's New Wave", ASM News, pp. 566–568 (1985). Previously, however, no solution has been forthcoming.

SUMMARY OF THE INVENTION

This invention provides a novel method of preparing complex polymers, including polypeptides and polynucleotides, wherein unreacted intermediates are attached to their supports at two locations and are thus removed from further reactions and from the final reaction product. This invention faciliates the production of polynucleotide sequences for use in biosynthetic reactions, expression and the like. Novel solid supports and other reagents are also provided.

In accordance with a preferred embodiment, methods of preparing a polypeptide are provided comprising an intermediate polypeptide covalently bound to a solid support. The intermediate polypeptide is then reacted with an amino acid moiety under conditions selected to covalently bond the amino acid moiety with the intermediate polypeptide. The reaction products are then exposed to further reaction conditions selected to effect covalent bonding of at least a portion of any unreacted polypeptide remaining after the peptidation step with the solid support. The result of the foregoing methods is that unreacted intermediate polypeptides become covalently bound or otherwise attached to the solid support in at least two locations, are "cyclized", whereas intermediate polypeptides which have successfully reacted with the further amino acid moiety remain bound to the solid support only through the original situs of binding, a terminal amino acid residue. As a result of this, upon successful elaboration of the polypeptide desired to be prepared, the materials on the solid support are exposed to conditions selected to cleave the terminal amino acid bond with the solid support. This cleaving frees the desired polypeptide since it is then no longer bound to the solid support. It may be recovered in accordance with conventional procedures. Those intermediate polypeptides which have failed in one of the desired peptidation steps and which, accordingly, have become covalently bound to the solid support more than one time remain bound to that support. Thus, a distinct, efficient and effective means for separating the desired products of solid state synthesis from the products of unwanted side reactions is obtained. The desired products are washed free of the support while the side products remain affixed to it.

In accordance with another embodiment of the present invention, the solid state synthesis of polynucleotides is facilitated through the use of reactions which cause unreacted intermediate polynucleotide to become doubly bonded to the solid support in a fashion analogous to that employed with polypeptides. Thus, in a preferred embodiment, a solid support having intermediate polynucleotide covalently or otherwise bound thereto is provided, and a nucleotide or blocked nucleotide moiety caused to react with the intermediate polynucleotide. Subsequently exposing the products of the reaction of the nucleotide moiety with the intermediate polynucleotide to reaction conditions selected to effect covalent bonding of at least a portion of any unreacted intermediate polynucleotide with the solid support is then performed forming a "cyclic" product; one attached to the support at least at two points.

As with the polypeptide embodiment, polynucleotide sequences which are successfully elaborated on the solid support in accordance with a preselected plan, are bonded to that support only through the intermediation of the first nucleotide residue. Intermediate polynucleotides which have failed to react with the further blocked nucleotide become doubly bonded, "cyclized", to the solid support, once through the first nucleotide residue and at least once through covalent bonding with the reactive bonding moieties. Upon subsequent cleavage of the covalent bond between the first nucleotide and the support, only end product is liberated from the solid support. Doubly-bonded, unwanted side products remain bonded to the support.

A preferred embodiment for accomplishing the cyclization of unreacted intermediate polypeptide or polynucleotide with the solid support employs selectively activatable bonding moieties attached to the solid support. After the reaction of a further amino acid moiety or nucleotide moiety with intermediate polypeptide or polynucleotide, an appropriate activatable bonding moiety on the solid support is chemically, photochemically, or otherwise activated into a species which is highly reacted with unreacted polypeptide or polynucleotide. Thus, for example, in the case of polypeptides, the reactive species thus formed can conveniently be reacted with an amino function which is generally resultant upon failure of a peptidation reaction. For polynucleotide synthesis, the activatable bonding moiety can be conveniently selected to be activatable into a species which is reactable with a free hydroxyl function as is generally resultant upon failure of intermediate polynucleotide cleotide to react with the additional nucleotide moiety. In any event, cyclization of the unreacted intermediate polypeptide or polynucleotide to the solid support results.

Other embodiments of this invention do not require a selectively activatable reactive bonding moiety on the solid support. Rather, the mixture of products and unreacted intermediate materials of a reaction step such as peptidation or nucleic acid elaboration may be exposed to reaction conditions designed to activate functions on unreacted intermediate peptides or nucleotides to form species reactive with the solid support. The reaction conditions are designed as not to effect properly-reacted polypeptides or polynucleotides. Thus, for example, in the case of peptides, unreacted intermediate peptide will typically have a free $NH_2$ (or COOH) group while the desired, augmented peptide has only blocked functions. Reaction conditions are selected to activate the amine (or acid) function, such as with phosgene, an amido chloride or other material to a reactive group such as a nitrene, an acide chloride, etc. The reaction is designed as not to effect the desired species on the support. The activated species then is allowed to react with the support or with moieties on the support to effect cyclization.

Unreacted intermediate polynucleotides will generally have an unreacted hydroxyl function while the desired polynucleotides will be fully blocked. Activation of such functions with, for example, methyl phosphodichloridite or trimethoxysilyl chloride to yield methyl phosphochloridite or trimethoxysilyl nucleotide or other reactive products leads to covalent reaction of the undesired species with the support or with moieties on the support.

Other polymeric species may also be synthesized in the solid state through the use of the present techniques. Complex polymers and polymers whose constituency must be carefully controlled, may be elaborated by analogy with the synthesis of polypeptides and polynucleotides. Thus, it is believed to be possible to prepare a strictly alternating copolymer, to synthesize molecules of biological interest, and possibly even to prepare materials whose availability is limited or impossible through traditional, organic chemical techniques such as nucleopeptides. In this regard, the method of using a second, selectively activatable and de-activatable bonding moiety covalently bonded to a solid support for solid state synthesis or the alternative oligomer activation embodiment permits unwanted side products to be covalently bonded to the solid support a different number of times from the desired reaction products to permit straightforward purification.

It is a principal object of this invention to provide methods for solid state synthesis of polypeptides, polynucleotides, and other oligomers, especially those of biological interest.

A further object of this invention is to provide methods for preparing pure synthetic polypeptides, polynucleotides, and other oligomeric molecules.

A further object is to provide methods for cost-effective preparation of polynucleotides or polypeptides.

Yet another object is to provide novel support media and reagents for solid state synthesis of polypeptides, polynucleotides, and other oligomers.

A still further object is to provide methods for the synthesis of oligomeric molecules which are amenable to automation and/or computer control.

Another object is to provide polypeptides through expression of polynucleotides prepared in accordance with the invention and to provide organisms having such polynucleotides included therein, especially in the genetic material thereof.

Still further objects will become apparent to those of ordinary skill in the art from a review of the present specification.

DETAILED DESCRIPTION OF THE INVENTION

Solid-state peptide synthesis was first proposed in the early 1960's by Merrifield and has subsequently become a well-known technique for the biochemist. Those of ordinary skill in the art are familiar with the general functioning of solid-state peptide synthesis together with basic knowledge of its reaction schemes and functions. Additional information is provided in the review articles which have been incorporated herein by reference. These provide disclosure as to the general techniques of solid-state peptide synthesis as well as insight into certain of the difficulties which have obtained heretofore in such synthetic schemes.

A wide variety of solid supports may prove to be useful in the practice of one or more embodiments of this invention. Any of those solid supports known to those of ordinary skill in the art will likely be useful. The traditional support used by Merrifield is a polystyrene polymer that has been cross-linked with divinylbenzene and then chloromethylated. The degree of cross-linking with divinylbenzene and of chloromethylation is variable but is normally between the ranges of 1%–2% and 1%–20%, respectively. Bromomethylated and iodomethylated variants of such resins have also been prepared. Alternatives to these resins include those with, for example, hydroxymethyl groups, which do not lead to alkylated side products such as have been seen with some polymers. One such resin has been prepared by treatment of the traditional-type resin with potassium acetate in hot benzyl alcohol and saponification of the resulting acetoxymethyl-resin with sodium hydroxide in ethanol See Bodanszky and Sheehan, *Chem. Ind.*, p. 1597 (1966).

An improvement to such polymers are polymers whose linkage to growing oligomer, e.g. peptide, is less acid-labile, the so-called PAM resin. This is an oxymethylphenylacetamidomethylated polystyrene resin or other kind of polystyrene-based support as reported in Mitchell et al., *J. Am. Chem. Soc.* 98, pp. 7357–7362 (1976) and Prystowsky et al., *Am. Pep. Symp., pp.* 349–352 (1979). Two other polymers that have been designed to release polypeptides containing carboxy-terminal amides are the benzhydrylamine and the 4-methylbenzyhydrylamine resins described in Pietta & Marshall, *J. Chem. Soc. D,* London, p. 650 (1970). Another resin that has been prepared particularly for use with peptides containing the very acid-labile 2-(4-biphenyl- 2-propyloxycarbonyl or Bpoc group is a styrene that has been cross-linked with divinylbenzene and p-alkoxybenzylhydroxylated. This is described in Wang and Merrifield, *Peptides*, Scoffone ed., pp. 74–83, N. Holland (1969). Another group of resins is the polyamide resins described by Atherton et al in *J. Am. Chem. Soc.* 97, pp. 6584–6585 (1970) and Smith et al., *Int. J. Pep. Protein Res.* 13, pp. 109–112 (1979).

Two further resins with improved properties of acid stability and greater flexibility in cleavage have complex groups inserted between the traditional polystyrene-based resin and the first amino acid residue and have been termed the POP and PON resins by Merrifield et al in *American Peptide Symposium*, pp. 29–47 (1979). Another resin described that may increase the effective degree of peptide per gram of resin is one patented by Bruce W. Erickson in U.S. Pat. No. 4,515,920. More than one peptide can be synthesized per originally chloromethylated group in accordance with such inventions. Other attachments to traditional resins include nucleophile-labile phenyl esters, Kenner and Seely, *J. Am. Chem. Soc.*, 94, pp. 259–3260 (1972); bromoacetyl esters, Weygand, *Peptides*, pp. 183–184 (1968); and sulfonylethyl esters, (Tesser et al., *Tetrahedron Lett.* 32, pp. 1069–1072 (1976)). Photolabile phenacyl esters, Wang, *J. Org. Chem.* 41, pp. 1350–1353 (1976); o-nitrobenzyl esters, Rich and Gurwara, *J. Am. Chem. Soc.* 97, pp. 1575–1579 (1975); acid-stable bromobenzyl esters and 4-trioxysilyl esters and the acid labile t-alkoxycarbonylhydrazideresin are also known. Numerous other functional groups have been introduced into or proposed for the traditional or other resins; many have been reviewed by Erickson and Merrifield, above. All of the foregoing may likely find utility in the practice of this invention. Other solid supports such as glass bead supports and carbohydrate supports reviewed by Erickson and Merrifield in *The Proteins*, Vol. 2, 3rd Ed., pp. 255–527 (1976) may be useful for some embodiments.

For nucleotide synthesis, some useful solid supports are polystyrene residue, usually with a lower degree of cross-linking than the Merrifield resin, Letsinger & Mahadevan, *J. Am. Chem. Soc.* 88:5319–5324 (1966) and polydimethylacrylamide to which a 2-hydroxy thioether, p-2-hydroxyethyl thiophenylpropionic acid has been attached via an amide linkage. Cleavage is effected by oxidation of the sulfide to the sulfone, followed by beta elimination. Polyacrylmorpholide, Narang et al., *Tetrahedron Lett.*, pp. 1819–1822 (1977), porous glass beads, and silica gel, Matteucci and Caruthers, *J. Am. Chem. Soc.* 103:3185 (1981), to which (3-aminopropyl) triethyloxysilane was attached by refluxing in dry toluene have been employed as well and may also be useful. The amino functional group was then reacted with succinic anhydride to generate a free carboxylic acid bound to the silica gel.

It is necessary to couple or covalently bond a first amino acid, nucleotide or other initial moiety to the solid support to serve as the basis or anchor for polymer elaboration. Preferably, the moieties are blocked for further augmentation reactions so as to avoid undesired side reactions. In the case of peptide synthesis, carbobenzoxy (benzyloxycarbonyl) (Cbz) or t-butyloxycarbonyl (Boc) amino acids can be satisfactorily coupled to the many resins, especially traditional resins, by refluxing in an organic solvent. Most of the traditional resin amino derivatives are commercially available. For example, hydroxymethylated resins can be coupled to the first amino-protected amino acid with N,N'dicylohexylcarbodiimide (DCC), N,N'-carbonyldiimidazole or with triphenylphosphine and 2,2'-dipyridyl sulfide or with other known coupling reagents. Since some of these activating agents are employed in the additional steps of the synthesis, these resins should be blocked after the first amino acid is attached. Bromoacetyl resins can be coupled to the first amino-protected amino acid salt usually at room temperature. The t-alkoxycarbonylhydrazide type solid supports can be coupled to the first amino-protected amino acid by DCC. See Wang and Merrifield, *J. Am. Chem. Soc.*, 91, pp. 6488 (1970).

For polypeptide synthesis, almost all prior successful solid phase peptide syntheses have used the solid phase as the carboxyl protecting group. This means that the amino acids that are to be added are blocked at the alpha amino function and at any relevant side chains. The most common alpha amino protecting groups are the previously mentioned Boc and Bpoc groups. These groups are readily cleavable in mild acid. The Cbz group requires stronger acid which could lead to scission of the peptide from the resin but may also be useful. The alternative removal of Cbz is with catalytic hydrogenation which uses a solid for a catalyst and which is often impractical with an already insoluble resin. Persons of ordinary skill in the art know the requirements and techniques for blocking in this context.

The sequence for chain growth for polypeptides consists of the following, exemplary, steps per cycle if the carboxyl terminus is bonded to the solid support. The resin with the alpha amino protected amino acid or peptide is deprotected. If necessary, the resin is neutralized with a tertiary amine and then the activated amino acid such as the N-hydroxysuccinimide ester or the nitrophenyl ester is added. At this point the excess activated amino acid is removed and the cyclization subroutine is begun. The latter consists of the addition of the condensing agent to the resin and the subsequent deactivation of the activated group. This sequence can be easily adapted to the automated system routinely used by the addition of the cyclization sub-routine. Removal of the peptide from the resin is conveniently done with anhydrous hydrogen fluoride. This normally also removes many of the protecting groups from the peptide.

Wallace et al. in *Solid Phase Biochemistry, ibid.*, describe typical synthetic routes or stages for nucleic acid synthesis on solid supports. Thus, it is known that a wide variety of supports are useful for such synthesis, especially modified polystyrenes, acrylamides, glasses and copolymers.

The initial nucleotide is usually attached to the solid support by its 3' end; synthesis proceeds from the 3' end to the 5' end of the nucleotide chain. Attachment can be conveniently accomplished by derivatizing an amine function on the solid phase with succinic anhydride to yield a carboxyl function which can be reacted with the 3' hydroxyl function on the nucleotide to form an amide. Subsequent cleavage is conveniently accomplished by reaction with ammonium hydroxide.

Because of the acid lability of carbohydrate groups, the final removal of oligonucleotides from the resin has been performed mostly under basic conditions. This generally has meant that the attachment to the solid support is via an ester that would be alkali removable. This would dictate that the protecting groups for the nucleotides or oligonucleotides to be added would be removably by mild acid. The best known and best used group for that are the trityl, methoxytrityl and dimethoxytrityl derivatives which can block the 5'-hydroxyl moiety. This means that addition of nucleotide or oligonucleotide is via the 3'-group, whether it is the phosphoryl (—$PO_4$), phosphoryl ester (such as the p-chlorophenyl ester), phosphite (—$PO_3$), the phosphite ester (such as the p-chlorophenyl ester), or otherwise. For example, the Merrifield polymeric resin and silica gel have been successfully derivatized with succinic acid and the first group added at the 3' or 5' hydroxyl groups with DCC. Alternatively, the polydimethylacrylamide linked to the 2-hydroxythioether can be reacted with the phosphate group of the first residue with a condensing reagent such as DCC.

The functional groups of the nucleotide are generally protected during synthesis. The protecting groups used in ordinary "wet" chemistry are generally suitable. The 5' hydroxyl is usually protected with a 4',4'-dimethoxytrityl group (DMT), while amine groups in the bases receive traditional protection, i.e. from benzoyl or isobutyryl substitution. Two major types of blocking groups have been used on solid supports. Those commonly used with Merrifield polymer resin have been the trityl, methoxytrityl and dimethoxytrityl groups which are easily removable with mild acid. The more common ones with polydimethylacrylamide are the acetyl and 2-cyanoethanol moieties, both of which are removable under basic conditions. The phosphate groups are protected by, e.g. aryl functions but numerous others have been used as well.

The nucleotide coupling reactions which are suitable for the practice of one or more embodiments of the invention may be any of those known to solution-phase biochemists. It is important to maximize yields of these reactions, however. The "phosphotriester" and "phosphite-phosphotriester" methods described by Wallace et al and known to those with ordinary skill in the art are presently preferred.

The sequence for chain growth may conveniently comprise the following steps per cycle. The resin with the 5'methoxytrityl group is deprotected with mild acid as discussed in part C. There are a number of condensing agents that have been used in oligonucleotide synthesis including DCC, mesitylenesulfonyl chloride, mesitylene nitrotriazole and 2,4,6-triisopropylbenzenesulfonyl dichloride. A condensing agent such as one of these is added along with the 5-methoxytrityl protected nucleotide. After the reaction is completed and the reagents are washed out, the cyclization subroutine is begun. This sequence can be easily adapted to the automated system currently in use by the addition of the cyclization sub-routine. Complete removal of the triester is effected by oximate treatment and removal of the nucleotide chain from the resin is brought about by base. The p-methoxy-trityl group is removed with mild acid and the purine and pyrimidine protecting groups are then removed with strong base.

In accordance with preferred embodiments, the solid support for the synthesis of peptides, nucleotides or other oligomers may be modified so as to have reactive bonding moieties present thereupon which are selectively activatable. Such moieties are activatable in a fashion such that they can be caused to react with unreacted intermediate peptide, nucleotide or other oligomer so as to cause incipient side products to be twice bonded to the support. This may be viewed as a type of cyclization. Thus, after some or all of the chain elongation routines, a cyclization subroutine is practical whereby the reactive group is activated, caused to react with unreacted intermediate product, and the balance deactivated for use in subsequent subroutine cycles.

The functional group that is to be used in the cyclizing sub-routine may be any of a wide variety of groups which can be bound to the resin and caused to react selectively as required. The activatable moiety should be insertable into the resin by a linkage that is not cleaved under conditions of normal removal and deprotection of finished polypeptides or polynucleotides. However, it should not react under normal coupling conditions. It should be selectively activatable and preferably, selectively de-activatable, if reaction has not occurred, in order to be usable in further cyclization sub-routines.

Preferred moieties with these characteristics which may likely be found to be useful during peptide synthesis are sarcosine (N-methylglycine). The addition of sarcosine to some traditional solid phase resins such as the Merrifield resin should yield tertiary amine with the free carboxylic acid. If the carboxylic acid competes as a nucleophile with the amine, sarcosine t-butyl ester can be added, followed by mild acid to remove the t-butyl ester. The degree of sarcosine substitution should probably be greater than the projected degree of peptide substitution in order to have the potential for efficient coupling of unreacted intermediate polypeptides or polynucleotides. Activation of the modified sarcosyl residue at the carboxyl group should be achievable with condensing groups used to activate protected amino acids, such as thionyl chloride or isobutyl chloroformate. Deactivation can likely be accomplished in mild base. Other examples or modifications will be apparent to those of ordinary skill in the art.

In a further, proposed, preferred embodiment, cyclization of unreacted peptides with the solid phase could be accomplished by activating, for example, free amine which remains upon failed peptide bond formation to a group that will react spontaneously with the resin or other solid support. An example of this would be the use of phosgene ($COCl_2$) which would add rapidly to a free amine to form an —NH—CO—Cl which could further react more slowly with hydroxyl groups on the resin, such as, for example, a hydroxymethylated resin, to effect cyclization. In such a case, it would be unnecessary to supply activatable groups on the resin, but only necessary to select a resin which is reactable with the type of reactive functionality selected for use with the intermediate product.

Activatable groups for use in the preparation of nucleotides, again, may be any of a wide variety of functions capable of being selectively activatable to react with unreacted intermediate product. In the case of nucleotides, such intermediate products generally have a free hydroxyl group. Thus, activatable groups on the support which, when activated, are reactive with the hydroxyls either directly or indirectly are preferred.

The activatable group that is to be used in the sub-routine may be bound to the resin or may be used to activate a hydroxyl or a hydroxyl derivative such as a carboxylic acid, an aldehyde or ketone or a halide to bind to a group that is on the resin. In the former case, the activatable group must be insertable into the resin by a linkage that is not cleavable under normal conditions of deprotection either of the intermediate or of the finished oligonucleotides or polynucleotides, does not react under normal coupling conditions of nucleotide or oligonucleotide conditions, can be selectively activatable and can be selectively de-activatable, if cyclization has not occurred, in order to be able to be usable in the next cyclizing sub-routine.

An example of this application is as follows: One can attach about 5-10% of the maximal amount of (3-aminopropyl) triethoxysilane to silica gel and further react it with succinic anhydride as mentioned above. See Matteucci & Caruthers, ibid. The other 90-95% of triethoxysilane-modifiable groups or the silica gel are reacted with (3-trifluoroacetylaminopropyl)triethoxysilane. The first residue such as the 5-methoxytritylnucleotide phosphotriester is condensed with the carboxylic acids as described above and excess carboxylic acid groups are blocked with DCC, p-nitrophenol and morpholine as described by Matteucci & Caruthers, above. The terminal nucleotide residue is deprotected by mild acid and the second residue added with a condensing agent. The cyclization sub-routine is preferably employed at this point such as the steps of removal of the trifluoroacetyl groups by mild base such as 1M piperidine, addition of a condensing reagent such as DCC with N-hydroxysuccinimide, and reprotection of the unreacted amino groups with trifluroacetyl anhydride.

In accordance with another embodiment, the free hydroxyl groups of unreacted intermediate polynucleotides can be reacted with a species to form a product which is reactable directly with amino groups on the support that can be generated by deprotection. An example of likely materials is methyl phosphodichloridite. Each of these schemes provides "cyclization" of unreacted intermediate nucleotides by two-fold covalent bonding with the support. Any other effective method may also be employed, however.

The advantages of the cyclization sub-routines are that they should provide a relatively simple, rapid, automatable procedure for trapping defective portions of a desired reaction sequence in a manner which will permanently separate the defective sequences from the released polymer of choice. This should prove to be invaluable in overcoming the major current disadvantage of the solid phase procedure; namely, the difficulty in the purification of large polymers from homologues of close molecular weight and similar structure.

The present invention provides a practical, easily usable series of chemical reactions that do not add to the number of unwanted side reactions. A particular advantage that this invention provides is that one of the "ends" of the materials to be joined by cyclization, the reactive groups on the resin, can be incorporated in great excess in order to facilitate contact with, for example, the unreacted amine. There is a precedent for a similar cyclization reaction dealing with protected peptides in the traditional solid phase resin which has been shown to occur in high yield. See Flanigan & Marshall, *Progress in Peptide Chemistry,* Vol. 2, Ed Lande, pp. 7-14 (1972). Merrifield in *Science* 232: 341, 1986 has pointed out that the volume of polystyrene-divinylbenzene resin swelled from a dry mass increased at least 25-fold in organic solvents. The resin and growing peptide chains are both highly solvated during the various reactions and are thus accessible to soluble reagents. In Merrifield's words "The reactions occur not only at the surface of the bead but, in major part, within the interior of the cross-linked polymeric matrix." This underscores the likely efficacy of inserting activatable moieties in and on, for example, polystyrene-divinylbenzene beads for the purpose of reacting them with amino peptide groups on growing peptide chains. Thus, unreacted sequences may be partially or completely buried in the resin, such that the amine to be reacted is placed precisely near the resin where cyclization is to take place, thus facilitating cyclization subroutines.

While certain embodiments of the present invention have been set forth, many other embodiments will also occur to those of ordinary skill in the art. Thus, while polypeptide synthesis has proceeded in accordance with a convenient method of attaching the carboxyl terminus of a growing polypeptide to solid support, analogous embodiments wherein the amino terminus is so attached are also comprehended hereby. A similar consideration attends the preparation of polynucleotides which can proceed from either the 3' or 5' terminus as desired.

The embodiments of the present invention may be employed in many ways during the preparation of polypeptides and polynucleotides and other polymeric material. Thus, the "cyclization" subroutine may be performed either once, a plurality of times, or during each step of polypeptide or polynucleotide synthesis. For example, it may be convenient to employ cyclization subroutines as disclosed herein with only one particular amino acid or nucleotide moiety to be included in growing polypeptide or polynucleotide chains. This would, for example, be most convenient when the particular amino acid or nucleotide moiety has demonstrated some particular difficulty in being completely reacted with the growing chain. Alternatively, and preferably, the cyclization subroutine may be employed after each peptidation or nucleotidal operation sequence, especially when autonomous preparative equipment is available for supervising the reaction sequences.

It is generally preferred to undertake the steps of reacting an amino acid or nucleotide moiety with a growing, intermediate polypeptide or polynucleotide under conditions selected to covalently bond the further moiety with the intermediate polymer followed by exposing the products of the reaction to further reaction conditions selected to effect covalent bonding of at least a portion of any unreacted intermediate polypeptide or polynucleotide remaining after the reaction step with a solid support a plurality of times in order to maximize the impact of the procedure upon the purity of the resulting polypeptide or polynucleotide. In this regard, it is expected that polypeptides and polynucleotides having improved purities over those available heretofore will result. Indeed, it is believed now to be possible to isolate a desired polypeptide or polynucleotide in substantially pure form or at least in a form from which purification may proceed without unacceptable interference from structrally similar by-products.

A chief benefit of this invention is purity in the preparation of important peptides such as growth hormones and proteins which should be an important step forward in the biotechnology needed by medicine and commerce. As new technologies involving designed proteins and polypeptide gene fragments are developed, the need for these synthetic materials will likely increase dramatically.

As those of ordinary skill in the art will appreciate, the present methods also provide means for preparing and isolating polynucleotides which are not heretofore available or which have been available only in admixture with other, similar materials. As such persons will appreciate, polynucleotides have found large utility in the various forms of genetic engineering known to those of ordinary skill in the art. It is known by such persons to employ polynucleotides in such a fashion that polypeptides may be derived therefrom. Thus, it is a specific object of this invention to provide polypeptides produced by expression of polynucleotides produced in accordance with one or more embodiments of the present invention. For example, such expression may comprise including a polynucleotide thus formed in the genetic material of an organism and by causing that organism to function to produce a peptide. As persons of ordinary skill in the art understand, there is a relationship between the sequence of polynucleotides and the identity of peptides produced through expression of those polynucleotides. Thus, it is believed now to be possible to preselect a polynucleotide for solid state synthesis in accordance with one or more of the present embodiments in such a fashion as to provide a preselected polypeptide through expression of the polynucleotide. The polypeptide resulting from these embodiments can be one which has not been available heretofore through any other method or one which has not been available in pure form or in useful quantities.

A further embodiment of the invention provides organisms which include in their genetic material polynucleotides produced in accordance with one of the embodiments of the invention. The techniques for such inclusion are known per se to persons of ordinary skill in the art and any such methods now known or hereafter devised may be used in conjunction with the embodiments of the present invention to prepare such organisms and to produce polypeptides through expression of the included genetic material of those organisms. Some of the biotechnological methodologies which may benefit from employment of polynucleotides produced in accordance with the embodiments of the present invention are described in *Biotechnology & Biological Frontiers*, Abelson ed., A.A.A.S. (1984), incorporated herein by reference.

It is to be understood that working examples have not yet been completed for this invention in view of the large time and expense requirements for their performance. Prophetic examples have been prepared based upon well-characterized, published solid state syntheses. While certain approaches are presented which are viewed as likely to succeed in securing one or more of the objects of the invention, other methods, reagents and practices will likely also prove to be useful.

EXAMPLE 1

Synthesis of staphylococcal nuclease and its trypsin digested fragments are generally described in Ontjes and Anfinsen, *Proc. Nat. Acad. Sci.* 64:428 (1969); Chaiken, *J. Biol. Chem.* 246:2948 (12971); Zeiger and Anfinsen, *J. Amer. Chem. Soc.* 5:880 (1973).

Staphylococcal nuclease is an enzyme with many advantages that make it amenable for solid phase synthetic studies. It has no disulfide groups to complicate its folding into an enzymatically active structure and its three dimensional configuration is known. It is cleavable by trypsin digestion in the presence of calcium and an inhibitor into three fragments called P1, P2 and P3. The two larger fragments, P2 (residues 6-48) and P3 (residues 50-149) can recombine to form nuclease-T, a complex with about 8% of the native activity. Solid phase synthesis has already been used to prepare the P2 fragment which has been purified to as high as 90% of the activity present in the natural P2 fragment. It should be stressed that activity per se is not a proof that the analogue has the correct amino acid sequence. The present invention offers an improvement over prior syntheses by holding promise of removing incorrect polypeptides that are close enough in sequence to the native enzyme to retain enzymatic activity and to interfere with purification of the desired species.

Prior attempts to synthesize the intact enzyme by solid phase synthesis have not met with particular success. The major difficulty has been the purification of the completed polypeptide. The present methods are intended to address the problem of deletion errors that accumulate in such a long synthesis. Since the original synthetic studies, a number of improvements in the solid phase synthesis of peptides have occurred and some of these will be incorporated in the proposed synthetic studies. The P2 fragment represents the previous model of success in solid phase peptide synthesis and is used as a comparative criterion for the effectiveness of the present improvements. P2 will be synthesized via the procedure of Ontjes and Anfinsen, as well as via two embodiments of the present invention. The relative enzymatic activities of the crude P2 preparations from each synthesis, when compared, are expected to reflect on the improvements while the enzymatic activities will be one measure of success. Others will include Edman degradation to detect the presence of preview sequences that denote synthetic deletions.

The Ontjes and Anfinsen approach will be done as reported. Reactions will be monitored in two ways. First, the carboxyl terminal amino acid that is attached to the resin will be $^{14}$C-labeled The radio labeled amino acid (proline for P2 and glutamine for P3 and nuclease) will be bought commercially and modified with the tert-butyloxycarbonyl (Boc) residue using well-known, commercially available reagents. The amount initially on the resin will be determined by hydrolysis of an aliquot of the amino acid-containing resin to the soluble amino acids, neutralization of the solution, addition to a scintillation solution and counting with a beta counter. By doing this periodically, the amount of peptide which has been lost from the resin during the synthesis can be calculated. Furthermore, by also treating aliquots of the resin with HF to remove uncyclized peptides and counting the amount of peptide released, we can tell how much of the peptides have been cyclized. This will be especially important at the end of the synthesis in assessing the value of the cyclization sub-routine.

In addition, the degree of completion of each reaction can be monitored via a test of an aliquot of resin with either (Kaiser et al., *Anal. Biochem.* 34:595, 1976), chlorninhydrin anil (Christensen, in *Peptides, Structure and Biological Function*, Gross and Meienhofer, Eds., Pierce Chem. Co., Rockford, Ill. p. 385, 1979) or Edman degradation to detect preview sequences. See R. A. Laursen, *J. Am. Chem. Soc.* 88:5344, 1966 and H. D. Niall et al., *Chemistry and Biology of Peptides*, J. Meienhofer, Ed., Ann Arbor Press, Ann Arbor, Mich., p. 695, (1972). In those cases, where the reaction is woefully incomplete, the coupling procedure can be repeated.

The attachment of Boc-$^{14}$C-proline to the resin be done at about 10% of the maximally reactable chloromethyl groups. Boc-$^{14}$C-proline is provided to the resin, excess radiolabeled reagent is removed followed by hydrolysis of the resin and counting of the liberated radioactive material. The 10%-modified resin will then be exhaustively reacted with sarcosyl-t-butyl ester to form the tertiary aminoacyl t-butyl ester. The sarcosyl t-butyl ester has not yet been made, but a likely synthetic scheme would envision starting with commercially available benzyloxycarbonylsarcosine and esterifying it under pressure in the presence of isobutylene. The resulting benzyloxycarbonylsarcosyl t-butyl ester will then be deprotected by hydrogenation over palladium and charcoal and attached to the resin. The subsequent addition of 4N HCl in dioxane, will remove both the Boc group on the proline and the t-butyl ester on the sarcosine.

The following amino acids will have their side chains protected: Lys, trifluoroacetyl; Arg, nitro; His, toluenesulfonyl; Asp, Glu, Tyr, Ser, and Thr; benzyl; and Met, sulfoxide. All of these protected amino acids are available from Bachem Chemical Co.

The routine for attaching an amino acid function to a growing peptide chain will consist of the following steps:

1. Neutralization of the HCl salt of the free amine with triethylamine and addition of the alpha-Boc-side chain protected amino acid preferably as the N-hydroxysuccinimide ester in 2.5-fold excess in dichloromethane. Active esters have to be added rather than employing dicyclohexyl carbodiimide, DCC, since the latter will activate the sarcosine residues. In the cases of Gln and Asn, the active ester is generally preferable in any event to the addition of DCC, since there is a reported side reaction associated with DCC addition (see review by J. M. Stewart in *Solid Phase Biochemistry*, Scouten, Ed., Ch. 10).

2. Washing out the excess monomer, testing for the degree of coupling and, if necessary, repeating the coupling until an acceptable degree of coupling has been achieved.

3. Addition of thionyl chloride in enough excess in methylene chloride at room temperature to activate sarcosyl residues attached to the resin but not enough to generate HCl sufficient to deprotect BOC groups. The sarcosyl chloride group will react with free amines from peptides that have not yet reacted, forming an amide that is covalently attached to the resin.

4. Washing out excess thionyl chloride and deactivating unreacted sarcosyl chloride back to the carboxylic acid with aqueous base in dioxane.

5. Washing the resin free of aqueous dioxane and deprotecting the alpha amine with 4N HCl in dioxane.

6. Washing out the excess HCl in dioxane and reequilibrating in a neutralization solvent.

Cleavage of the peptides from the resin will be with HF for 1 hour at 0° C. in the presence of anisole (Ontjes and Anfinsen, Proce. *Natl. Acad. Sci.* 64:428, 1969) followed by 1M piperidine and 8M urea to remove trifluoroacetyl groups. It is expected that peptide subunits produced employing embodiments of the present invention will be obtained with greater purity and ease of isolation.

EXAMPLE 2

The second synthesis will utilize the 4-(oxymethyl) phenylacetamidomethyl-1% divinylbenzene cross-linked polystyrene or PAM resin described by Mitchell et al. in *J. Org. Chem. Soc.* 43:2845, (1978), whose constituent starting materials are commercially available (Pierce Chemical Co.). This resin is much more acid stable than the Merrifield resin and consequently will leach off much less peptide during the course of synthesis.

The preparation of the solid phase will utilize aminomethyl-1% divinylbenzene cross-linked polystyrene beads for attaching the first amino acid residue. For the synthesis of the P2 fragment, Boc-$^{14}$C-proline will be coupled to 4-bromo-methylphenyl acetic acid phenacyl ester and the resulting Boc-proline-4-oxymethylphenyl acetic acid phenacyl ester treated with Zn in acetic acid to remove the phenacyl ester. The amount of amine in the resin will be determined by Kjeldahl nitrogen analysis and about 0.1 equivalents of Boc-proline-4-oxymethylphenyl acetic acid per aminomethyl group on the resin added with 0.1 equivalent N,N'-dicyclohexylcarbodiimide (DCC). After washing out excess reagents, the remainder of the amines will be reacted with a large excess of succinic anhydride, forming an HF-insensitive amide bond and leaving carboxylic functional groups for every amine that had reacted. In the cyclization format, the unreacted amines will react with the thionyl chloride activated carboxylic acids on the resin, resulting in the cyclization to HF-insensitive amide bond.

The various steps in synthesis, cyclization (activation, reaction, deactivation) and deblocking have already been outlined in connection with Example 1. It is expected that the polypeptide thus prepared will have excellent purity.

EXAMPLE 3

D. M. Matteucci and M. H. Caruthers, *J. Amer. Chem. Soc.* 103:3185 (1981) describe the general procedure after which this example is patterned. They report a yield of deoxydecanucleotide of 30% for the synthesis of the sequence d(C-G-T-C-A-C-A-A-T-T).

This synthesis of Matteucci and Caruthers will be repeated The silica gel and protected nucleosides (5'-O-dimethoxytrityl derivatives of N-isobutyryl deoxyguanosine, N-benzoyl deoxyadenosine and N-benzoyl cytidine which have been activated to the 3'-0-methoxy-tetrazoylphosphine) used by Matteucci and Caruthers will be used as well. The silica gel will be derivatized by 3-aminopropyl-triethyloxysilane as reported and further modified by 0.1 equivalents of succinic anhydride to form an amide with a free carboxylic acid group. The remainder of the amines and any excess silanol groups will be capped. The initial reaction of the 3'-terminal deoxythymidine to the modified silica gel with DCC as well as subsequent cyclization reactions will be monitored with $^{14}$C-labeled 5'-0-dimethoxytrityl-deoxythymidine. The latter is to be prepared by the addition of dimethoxytrityl chloride to the commercially available radiolabeled nucleoside.

Excess amino and silanol groups must be deactivated during the course of the synthesis. One method which was used by Matteucci and Caruthers is to deactivate them throughout the course of synthesis. If the deactivation of amino and silanol groups is irreversible, it is unlikely that the cyclization sub-routine can use the same silica gel beads. Fresh beads may be added to form the second base-insensitive bond in such a case. A more flexible approach is to deactivate the amino groups with a selectively removable and reformable protecting group.

An example where silanol and amine groups have been deactivated with trimethylsilyl chloride employs trimethoxysilyl chloride to deactivate the unreacted 5'-hydroxyl groups of potential deletion sequences. At the end of the synthesis, fresh silica gel beads can be added to react with the trimethoxysilyl groups to form a silica gel adduct similar to the first reaction in which the 3-propyl amino group was introduced into the resin. An alternative approach is to cap both the silica gel and unreacted 5'-hydroxyl groups with trimethoxysilane and to heat the mixture with neutralized silicate to form cyclic products.

There are numerous protecting groups that can be used for amino and hydroxyl moieties that are on the resin. Their removal, however, should, in accordance with this embodiment, be selective with 5'-O-trityl groups (acid and reduction sensitive) and nucleotide base protecting groups (base sensitive) present on the oligonucleotide molecule. Two possible protecting groups inter alia will likely be useful. The first is the chloroacetyl group which is removable under mild conditions with thiourea or substituted thioreas. See Masaki et al., *J. Amer. Chem. Soc.* 90:4508, (1968). One potential problem is that the alkyl halide, can possibly react directly with free hydroxyl groups under basic conditions. This will pose no problem if the free hydroxyl is on an unreacted 5'-hydroxyl group (i.e., where the correct sequences are trityl protected), since the ether bond formed is expected to be stable to conditions of removal of the completed polynucleotide from the silica gel. The second proposed protecting group is the trimethylsilyl group that was used by Matteucci and Caruthers. This group is reported by Birkofer et al. (*Chem. Ber.* 94:821, 1961) to be very labile in methanol.

The protected mononucleotides will be activated to the phosphite with methyl phosphodichloridite and then to the methyl phosphotetrazole as reported by Matteucci and Caruthers.

There are three sequences of steps that may be likely be employed. The first set of sequences is to be employed when the silica gel is capped for the entire synthesis with trimethylsilane.

1. Removal of the 5'-O-dimethoxytrityl group with mild acid.
2. Washing and adding excess activated protected nucleotide methyl phosphotetrazole. This step will be repeated to raise the yield.

These steps are followed by:

3. Washing out excess activated monomer and adding trimethoxysilyl chloride for future cyclization. The product, 5'-O-trimethoxysilyl protected nucleotide, resembles the 3-aminopropyl trimethoxysilane group that was bound to silica gel in the first step. At the end of the synthesis, either before or after the completed deoxydecanucleotide is removed from the silica gel, oligonucleotides with the trimethoxysilane is caused to be bound to fresh silica gel beads. A variation of this approach would be to have capped the amines on the silica gel with trimethoxysilane groups, to react unreacted 5'-hydroxyl groups on the nucleotide with trimethoxysilyl chloride and to link the two chains at the end of the synthesis with silicic acid or methyl silicates. Under these conditions, the correctly synthesized deoxynucleotides will remain in solution, whereas those that reacted with the trimethoxysilyl chloride will remain on silica gel.

4. Washing out excess trimethoxy silyl chloride and oxidation of the phosphite to the phosphate with iodine, 2,6-lutidine and tetrahydrofuran as known.

The second proposed set of sequences will use the silica gel having chloroacetyl protected amino groups. The first two steps are identical to those above.

1. Removal of the 5'-O-dimethoxytrityl group with mild acid.
2. Washing and adding excess activated protected nucleotide methyl phosphotetrazole. This step will be repeated to raise the yield.

3. Washing out excess activated monomer and adding excess methyl phosphodichloridite. Deoxynucleotides with a free 5'-hydroxyl will react to form the 5'-O-methylphosphochloridite group.

4. Washing out excess methyl phosphodichloridite and adding thiourea in dioxane to generate the free amino groups on the silica gel.

5. Washing out excess thiourea and allowing the free amine to react with available 5'-O-methyl phosphochloridite groups (neutralization of the amine with triethylamine may be necessary).

6. Reprotection of the amino groups with chloroacetyl chloride or anhydride and washing out excess reagent.

7. Washing out excess reagent and iodination of the methylphosphite groups to the methyl phosphate groups as mentioned above. Iodination of chloroacetyl groups to iodacetyl groups should not change any of the reactivities significantly.

It is expected that the polynucleotide thus prepared will have very high purity and activity.

What is claimed is:

1. A method of preparing a polynucleotide comprising:
   (a) reacting a nucleotide moiety with an intermediate which has a 3' hydroxyl end a 5' hydroxyl end and which is covalently bound to a solid support at a first hydroxyl end of said intermediate polynucleotide under conditions selected to covalently bond the nucleotide moiety with the intermediate polynucleotide, and;
   (b) exposing the products of step (a) to reaction conditions selected to effect covalent bonding of at least a portion of any unreacted intermediate polynucleotide remaining after step (a) with the solid support at a second hydroxyl end of said intermediate polynucleotide.

2. The method of claim 1 further comprising performing steps (a) and (b), sequentially, a plurality of times with a preselected series of nucleotide moieties to produce a preselected polynucleotide.

3. The method of claim 1 further comprising isolating the polynucleotide thus prepared.

4. The method of claim 1 wherein the solid support has selectively activatable bonding moieties bonded thereto.

5. The method of claim 1 wherein the exposing step comprises reacting a free hydroxyl function on unreacted intermediate polynucleotide with an activating material to form a chemical species reactable with the solid support.

6. The method of claim 1 performed under autonomous control.

7. The method of claim 3 wherein the isolation comprises cleaving the covalent bond at said first hydroxyl end under conditions which substantially do not cleave the covalent bond at the second hydroxyl end.

8. The method of claim 4 wherein the selectively activatable bonding moieties comprise (3-aminopropyl) triethoxysilyl moieties reacted with succinic anhydride.

9. The method of claim 4 wherein the exposing step comprises selectively activating the bonding moieties to form species reactive with the intermediate polynucleotide.

10. The method of claim 5 wherein the activating material is methyl phosphodichloridite.

11. A method of preparing a polynucleotide comprising:

bonding a first nucleotide moiety having a 3' hydroxyl end and a 5' hydroxyl end to a solid support through a first hydroxyl end;

reacting a series of further nucleotide moieties with the first nucleotide moiety bound to the solid support to form an intermediate polynucleotide having a 3' hydroxyl end and a 5' hydroxyl end covalently bound to the support at a first hydroxyl end of said intermediate polynucleotide;

reacting an additional nucleotide moiety with the intermediate polynucleotide under conditions selected to covalently bond the additional nucleotide moiety with the intermediate polynucleotide; and exposing the products of the preceding step to reaction conditions selected to effect covalent bonding of at least a portion of any unreacted intermediate polynucleotide remaining after the reaction of the preceding step with the solid support at a second hydroxyl end of said intermediate polynucleotide.

* * * * *